United States Patent
Kraus

(10) Patent No.: US 11,504,166 B2
(45) Date of Patent: Nov. 22, 2022

(54) IMPLANT FOR THE STABILIZATION AND/OR FUSION OF THE SACROILIAC JOINT AND METHOD FOR FIXING THE SACROILIAC JOINT

(71) Applicant: Kilian Kraus, Werneck (DE)

(72) Inventor: Kilian Kraus, Werneck (DE)

( * ) Notice: Subject to any disclaimer, the term of this patent is extended or adjusted under 35 U.S.C. 154(b) by 111 days.

(21) Appl. No.: 16/740,986

(22) Filed: Jan. 13, 2020

(65) Prior Publication Data

US 2020/0222088 A1 Jul. 16, 2020

(30) Foreign Application Priority Data

Jan. 11, 2019 (EP) .................................. 19151394

(51) Int. Cl.
*A61B 17/70* (2006.01)
*A61B 17/84* (2006.01)

(52) U.S. Cl.
CPC ........ *A61B 17/7055* (2013.01); *A61B 17/846* (2013.01)

(58) Field of Classification Search
CPC .............. A61B 17/7055; A61B 17/846; A61B 17/7098; A61B 17/864; A61B 17/8625
USPC .................................. 606/246–249, 300–330
See application file for complete search history.

(56) References Cited

U.S. PATENT DOCUMENTS

| | | | |
|---|---|---|---|
| 7,922,765 B2 | 4/2011 | Reiley | |
| 9,308,034 B2 * | 4/2016 | Grady, Jr. | ............. A61B 17/74 |
| 9,675,398 B2 | 6/2017 | Kraus | |
| 2001/0012966 A1 | 8/2001 | Studer et al. | |
| 2007/0270879 A1 * | 11/2007 | Isaza | ................... A61B 17/1742 606/104 |
| 2009/0024174 A1 * | 1/2009 | Stark | ................... A61B 17/8625 606/321 |
| 2011/0294094 A1 * | 12/2011 | Moshavi | ............... A61C 8/0022 433/174 |
| 2015/0045892 A1 * | 2/2015 | Lynn | ...................... A61F 2/4601 623/17.16 |
| 2018/0271664 A1 | 9/2018 | Hermle | |
| 2019/0290341 A1 * | 9/2019 | Loftus | ................. A61B 17/8625 |
| 2019/0343565 A1 * | 11/2019 | Tempco | ................ A61B 17/866 |
| 2020/0155210 A1 * | 5/2020 | Huwais | ................ A61B 17/863 |

FOREIGN PATENT DOCUMENTS

| | | |
|---|---|---|
| DE | 102015121658 A1 | 6/2017 |
| EP | 1818025 A2 | 8/2007 |
| WO | 2006020463 A1 | 2/2006 |
| WO | 2011048140 A1 | 4/2011 |
| WO | 2019020690 A1 | 1/2019 |

\* cited by examiner

*Primary Examiner* — Eduardo C Robert
*Assistant Examiner* — Tara Rose E Carter
(74) *Attorney, Agent, or Firm* — Laurence A. Greenberg; Werner H. Stemer; Ralph E. Locher

(57) ABSTRACT

An implant for the stabilization and/or fusion of the sacroiliac joint has an elongated, spiraled exterior shape. The implant has a conically tapered inner core with a passage opening which extends in the axial direction along a central longitudinal axis over the entire axial length of the implant and ribs which run outward in a radial manner at least sectionally and which are arranged on the inner core and extend helically in the axial direction around at least one section of the inner core.

20 Claims, 10 Drawing Sheets

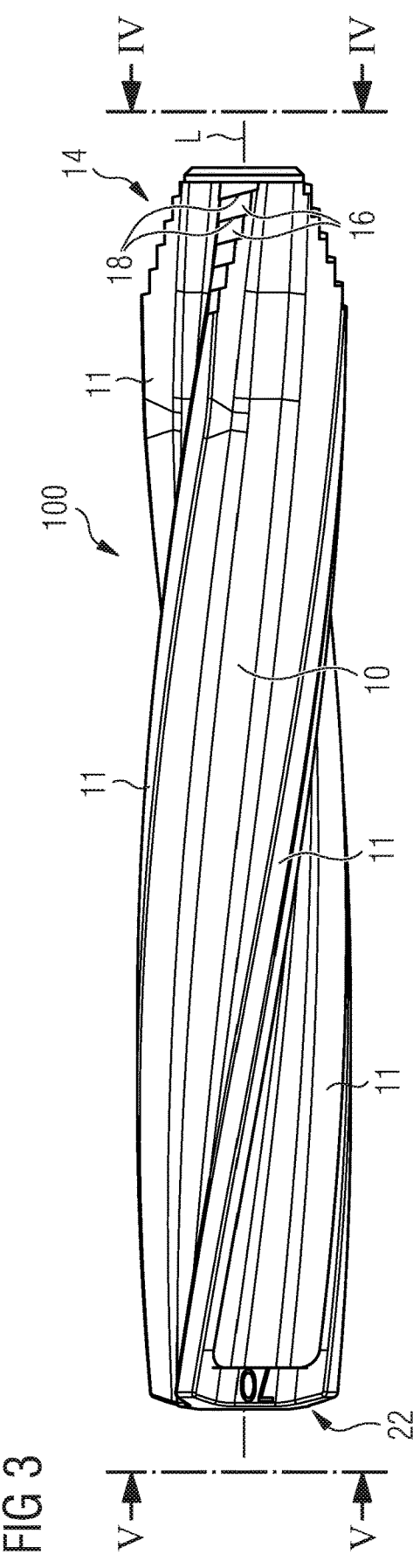
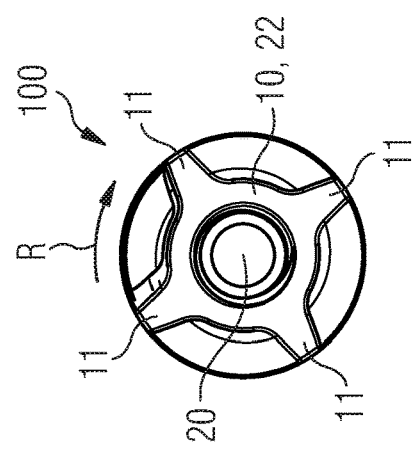
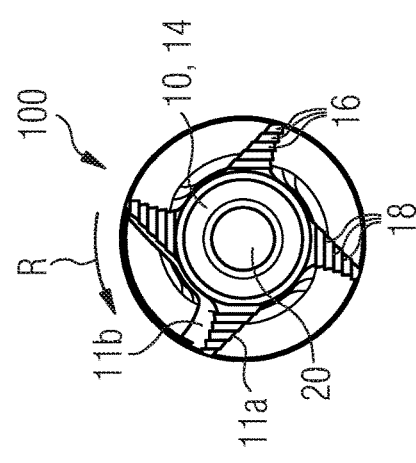

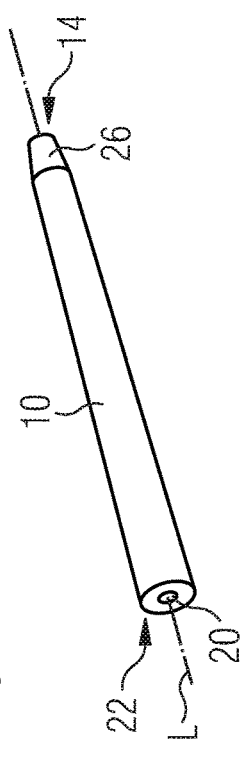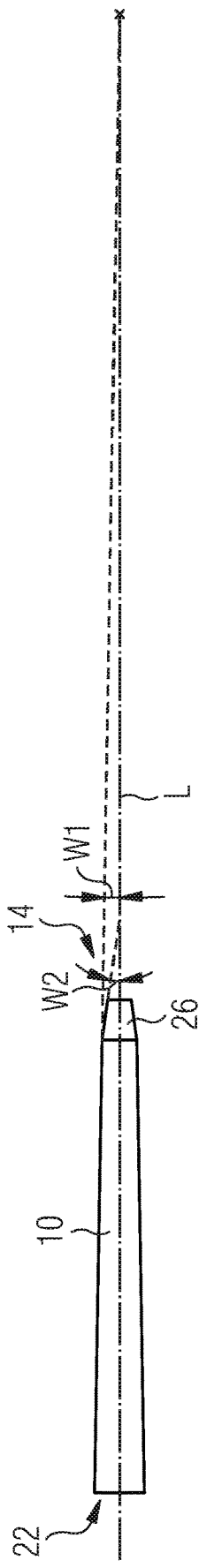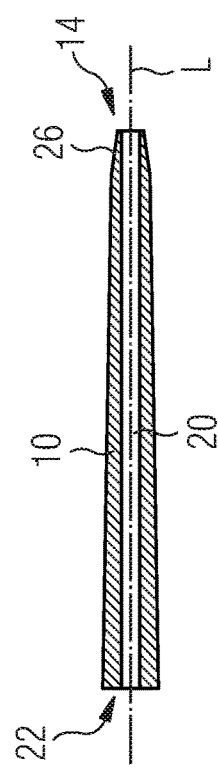

IMPLANT FOR THE STABILIZATION AND/OR FUSION OF THE SACROILIAC JOINT AND METHOD FOR FIXING THE SACROILIAC JOINT

CROSS-REFERENCE TO RELATED APPLICATION

This application claims the priority, under 35 U.S.C. § 119, of European patent application EP 19151394, filed Jan. 11, 2019; the prior application is herewith incorporated by reference in its entirety.

BACKGROUND OF THE INVENTION

Field of the Invention

The invention relates to an implant for the stabilization and/or fusion of the sacroiliac joint and to a method for fixing the sacroiliac joint.

The sacroiliac joint (Latin: Articulatio sacroiliaca) is a joint of little movement that is formed between the sacrum (Latin: Os sacrum) and the left or right ilium (Latin: Os ilium). In the event of a fracture or in the event of pain attributable to the sacroiliac joint, it is often appropriate from a medical standpoint to fix and/or to fuse the bone fragments or else the bones forming the sacroiliac joint by means of implants. For this purpose, pin-like implants, which are inserted into the bones or bone fragments to be connected, are known in particular from the prior art.

For example, U.S. Pat. No. 7,922,765 B2 describes pin-like implants which can have especially a shape, such as, for instance, a triangular cross section or the like, for preventing a rotation around the longitudinal axis of the implant.

To be able to insert such implants, it is first necessary to introduce appropriately dimensioned recesses into the bone fragments or bones to be connected. This is typically done by drilling and/or chiseling.

To fix the sacroiliac joint, it is especially known to provide multiple pin-like implants next to one another, with each implant running substantially transversely to the sacroiliac joint and bridging the adjacent joint surfaces. In the case of a commercial implant system, the pin-like implants are positioned by a cannulated insertion system, in which the implants provided with a passage opening are slid on previously introduced guide pins.

SUMMARY OF THE INVENTION

It is an object of the invention to provide an implant for the stabilization and/or fusion of the sacroiliac joint that ensures a stable fixation and can be used especially as part of a minimally invasive surgical procedure.

This object is achieved by an implant for the stabilization and/or fusion of the sacroiliac joint having the features of the independent claim.

Advantageous embodiments are subject matter of the dependent claims.

An implant for the stabilization and/or fusion of the sacroiliac joint, having an elongated, spiraled exterior shape, contains a conically tapered inner core (also: internal body, internal core) having a passage opening which extends in the axial direction along a central longitudinal axis over the entire axial length of the implant and ribs which run outward in a radial manner at least sectionally and which are arranged on the inner core and extend helically in the axial direction around at least one section of the inner core.

The implant has a spiraled exterior shape owing to the ribs which extend helically around the inner core and around the central longitudinal axis. The implant is therefore generally introduced into the bone material under a rotation. A translatory movement of the bone parts connected by the implant according to the invention in the direction of the central longitudinal axis is therefore associated with a corresponding counter movement in the opposite direction of rotation or with significant displacement of bone material. However, a relative rotation of the two connected bone parts can, for example, be blocked effectively if, instead of just a single implant being used for the fixation of the bone parts, multiple implants designed in such a manner are arranged next to one another. The use of multiple implants having a spiraled (also: twisted) exterior shape in each case thus advantageously increases implant stability especially in the case of the fixation or stabilization of the sacroiliac joint.

The inner core extends along the central longitudinal axis of the implant and can generally differ especially with respect to its cross section. According to the invention, the inner core is conically tapered around the central longitudinal axis with rotational symmetry and especially in the direction of a first end. In other words, the inner core of the implant tapers toward the first end. This simplifies the insertion of the implant and reduces especially the need to remove bone material to a significant extent prior to insertion in order to be able to correctly place the implant. Conically tapered inner cores facilitate especially the direct introduction of the implant into bone material, for example by striking or hammering. In this case, the first end is to be oriented in the driving direction when using the implant as intended, i.e., the implant is introduced or driven into the bone material with the conically tapered end first. The implant is configured to be directly introduced into the bone material of the bones or bone fragments to be fixed. This is to be especially understood to mean that no removal of material or an only slight removal of material, for example by drilling or chiseling, is necessary before the insertion of the implant. Any possible removal of material is preferably done for better positioning of the implant. In embodiments, the implant can, for example, be directly struck into the bone. For correct positioning of the implant, use can made of especially a guide pin or guide wire, which is first introduced at the site of implantation and is then inserted into the passage opening of the implant.

In possible embodiments, the number of radially protruding ribs (also: wings) differs. In preferred embodiments, three to five radially protruding ribs are arranged on the inner core, for example.

In embodiments, the maximum gradient of the conically tapered inner core is just a few percent, preferably approximately 1%. Based on the opening angle of the conically tapered inner core, this means that, in embodiments, the opening angle is preferably not more than a few degrees, particularly preferably less than 1°, for example 0.5°. The above-defined gradient corresponds to the tangent of the opening angle. The size of the opening angle is, then, based on the central longitudinal axis.

In embodiments, the inner core has, in the region of the first end, a centering tip which forms a terminally conically tapered section. The opening angle of the centering tip differs from the opening angle of the conically tapered inner core and is generally larger than the latter. In embodiments, the opening angle of the centering tip—based on the central longitudinal axis of the implant—is less than 20°, preferably less than 15°.

In embodiments, the ribs taper in the region of the first end in the direction toward the central longitudinal axis. Such optional embodiments serve, too, to allow or to facilitate the direct driving of the implant, especially by striking, as already described above.

In embodiments, the ribs have, in the region of the first end, a terminal section having a stepped profile. The stepped profile forms multiple cutting edges which further simplify the driving of the implant into the bone material.

In embodiments, the stepped profile contains multiple steps, the widths of which increase in the circumferential direction in the direction of the first end.

In embodiments, the ribs form a right-handed helix and the stepped profile contains at least one step edge (also: cutting edge) which, with regard to the axial direction and a circumferential direction, runs diagonally such that a right-hand twist is brought about when the terminal section is axially driven into bone material. Alternatively, the ribs form a left-handed helix and the stepped profile comprises at least one step edge which, with regard to the axial direction and a circumferential direction, runs diagonally such that a left-hand twist is brought about when the implant is axially driven in the direction of the terminal section into bone material. In other words, the at least one step edge of the stepped profile is oriented against the direction of rotation of the ribs in the driving direction, with the result that, when the implant is axially driven in the direction of the central longitudinal axis, what is brought about according to the principle of action and reaction is a force component which results in a torque in the direction of rotation of the helical ribs. What is thus achieved is that, when simply driving into the bone material, the implant is brought to a rotation which facilitates further driving.

In embodiments, the inner core and/or the ribs is/are perforated and/or provided with a channel structure. In preferred embodiments, the implant has a channel structure containing a multiplicity of open channels. By preference, the channels each have a cross-sectional area of from 8,000 $\mu m^2$ to 7,000,000 $\mu m^2$, preferably a cross-sectional area of from 50,000 $\mu m^2$ to 3,100,000 $\mu m^2$, particularly preferably a cross-sectional area of from 125,000 $\mu m^2$ to 570,000 $\mu m^2$. A channel structure dimensioned in such a manner is matched with the capillary action of blood and thus promotes the penetration of blood into the implant to a sufficient depth. As a result, support is advantageously given to the adherence of the intervertebral implant with adjacent bones. In other embodiments, the perforation and/or the channel structure serves to anchor the implant in the bone by cement, especially bone cement or bone substitute material, introduced, especially injected, into the implant.

In embodiments, the channel structure is honeycombed, latticed or meshed. Such embodiments allow the penetration of natural bone material and/or the introduction of bone substitute material and/or filling materials, such as cement in particular, for example bone cement, and are subjectable to high mechanical stress.

In embodiments, the channel structure has at least one outwardly open channel which provides a fluidic connection to the passage opening. An implant configured in such a manner is especially intended to be filled in with filling material, such as, for instance, cement or artificial bone material, after insertion into the bone parts to be connected. The curable filling material injected, for example, into the passage opening can escape especially across the channel or the channels of the channel structure in order to anchor the implant in the bone material. Such variants of the invention can improve the stability of the implant and are suitable especially for use in osteoporosis or in other cases in which the natural bone material exhibits a reduced bearing capacity or a reduced capacity for depositing new bone tissue can be assumed.

In a further development, the implant is closable by a closing element in the region of the first end. The closing element is, for example, a type of plug which can be inserted into the tip of the implant, especially through the passage opening, and anchored there. To this end, the closing element and the passage opening are, for example, provided with threads. The closure of the end of the passage opening considerably benefits the escape of the subsequently filled filling material especially across the channels or the channel structure in order to combine with the surrounding, natural bone material.

The implant is intended to be in direct contact with bone material, especially at least sectionally with the sacrum and/or the ilium. In advantageous embodiments, the inner core and/or the ribs has/have a surface structuring, for example in the form of multiple protruding projections. The surface structuring has a specified roughness which is especially within the micrometer range, submicrometer range and/or within a range from 10 µm to 100 µm. The aim thereof is to reduce or prevent especially movements of the implant after it has been inserted. The micrometer range is especially understood to mean the range between 1 µm and 10 µm. The submicrometer range is especially understood to mean the range between 100 nm and 1 µm. The expression that the surface structuring has a specified roughness within a certain range is to be especially understood to mean that a parameter characterizing the roughness of the surface structuring, such as, for instance, the area-based roughness value $S_a$, assumes a value within the relevant range, i.e., assumes for example a value between 100 nm and 1 µm for a surface structured within the submicrometer range, a value between 1 µm and 10 µm for a surface structured within the micrometer range or a value between 10 µm and 100 µm for a surface structured within the large micrometer range. The surface structuring can be generated especially by additive or subtractive processes. Especially when the implant is produced by means of an additive production process, such as, for instance, selective laser sintering or selective laser melting, the surface structuring can already be generated during production. Surface structurings produced in such a manner are typically within the large micrometer range between 10 µm to 100 µm and can have especially a regular structure in the form of grooves, ribs or teeth. The production of smaller surface structurings is preferably done by subtractive or additive processes, such as, for instance, coating processes or deposition processes, which are distinguishable from the additive production processes. Subtractive processes suitable for surface structuring encompass especially etching or treatment of the surface with a jet of abrasive particles. Surfaces structured in such a manner typically have randomly distributed, preferably homogeneously distributed elevations and/or depressions. The etched or abrasive-treated, metallic or nonmetallic surfaces of the implant preferably have a high purity especially with respect to contamination with foreign atoms in order to promote hydrophilic properties of the surfaces or the integration of the implant in the bone. To this end, it is possible to use especially high-purity acids in etching or to provide an etching operation after the treatment of the surfaces with abrasive particles in order to clean them of blasting agents.

In embodiments, the surface structuring contains, at least regionally, deposits consisting of a nonmetallic material, especially of an osteoconductive and/or hydrophilic material. Such deposits are produced especially by additive processes or by treatment of the surface with nonmetallic particles consisting of, for example, an osteoconductive and/or hydrophilic material. The deposits can, for example, be formed by planar coatings which form, sectionally or completely, especially the outer surface of the implant. In other cases, the deposits are formed by local single-crystal deposits or by treatment of the surface with particles composed of appropriate nonmetallic material. The deposits consist for example, at least in part, of calcium phosphate, a hydroxyapatite and/or a ceramic.

Alternatively or additionally, the inner core and/or the ribs is/are, for example, porous, especially open-cell porous, in order to allow an ingrowth of bone material. In particular, the above-described channel structure can be formed by the core and/or the ribs being porous. In other embodiments, the contact surfaces are substantially smooth.

In embodiments, the ribs extending helically around the central longitudinal axis have a constant thread pitch.

In embodiments, the ribs extending helically over the axial length of the implant wind around the central longitudinal axis over an angular range of less than 180°, preferably over an angular range between 45° and 120°, particularly preferably over an angular range of about 90°. The thread pitch is thus—in comparison with conventional screw implants which are driven into the bone material by exertion of a torque—relatively flat in order to allow a direct striking or hammering of the implant into the bone parts to be connected.

In embodiments, the ribs have a rectangular or trapezoid shape in the cross section perpendicular to the central longitudinal axis. In particular, in possible embodiments, the ribs have in cross section the shape of an isosceles trapeze.

In embodiments, the passage opening has, in the region of a second end arranged opposite the first end, an internal thread for the screw-in of an implantation tool. Such embodiments allow especially the subsequent removal of the already inserted implant by an implantation tool which has a corresponding external thread and which can be screwed into the internal thread introduced terminally into the passage opening.

In embodiments, the ribs are regularly spaced from one another in the circumferential direction. In exemplary embodiments having two radially protruding ribs, these are accordingly preferably arranged diametrically in relation to one another. In exemplary embodiments having more than two ribs, these are preferably arranged with a regular distribution around the circumference of the inner core. In such embodiments, the implant has, for example, a star-shaped cross section.

In embodiments, the implant is formed, at least in part, of a metal or a metal alloy, especially a titanium alloy. Preference is given to so-called grade 5 alloys, especially Ti-6Al-4V, which is distinguished by high strength and resistance. In other embodiments, the metal or the metal alloy consists of titanium, zirconium, oxidized zirconium, hafnium, platinum, rhodium, niobium, medical-grade stainless steel, cobalt-chromium steel or tantalum.

In embodiments, the volume of the ribs to a displacement volume is in the ratio of from 1/10 to 1/2 (alternatively written: 1:10 or 1:2), preferably in the ratio of from 1/5 to 1/2 (alternatively written: 1:5 or 1:2) and particularly preferably in the ratio of about 1/3 (alternatively written: 1:3). Here, the displacement volume is defined by the difference between the volume of a rotation body, which arises by continuous rotation of the implant around the central longitudinal axis, and the volume of the implant. The displacement volume characterizes the volume of the bone material which would have to be removed in order to remove the implant by translation in the direction of the central longitudinal axis. The displacement volume substantially corresponds to the volume of the gaps which are delimited, in the circumferential direction, by the radially protruding ribs and, in the radial direction, by the core and by the rotation body enveloping the implant. Implants geometrically dimensioned in such a manner are adapted to the compressive strength of bone material depending on the materials of which the implant consists. Lower ratios of not more than 1/5 are particularly preferred especially in the case of implants which consist, at least in part, of titanium or a titanium alloy and are produced by means of an additive manufacturing process, since it has emerged that implants produced in such a manner have a reduced fatigue strength.

In the case of implants, the radial extents of which exhibit only little change along the central longitudinal axis, the above-specified ratio of volume of the ribs to displacement volume can also be defined approximately on the basis of cross-sectional areas. In this case, the above-defined ratio corresponds to the ratio of the cross-sectional area of the ribs (i.e., the cross-sectional area of the implant minus the cross-sectional area of the inner core) to the surface area of a circular disk enveloping the maximum cross-sectional diameter of the implant. The maximum cross-sectional diameter is defined especially by the maximum radial extent of the ribs sticking out radially from the inner core. Here, cross-sectional area is especially considered to be the sectional area of the implant in the case of a cross section perpendicular to the central longitudinal axis. Irrespective of the specific geometric shape of the cross-sectional area, the diameter of the enveloping circular disk is always chosen such that the cross-sectional area is completely within the enveloping circular disk. The enveloping circular disk is especially the circular disk with the smallest radius or diameter, for which the cross-sectional area of the implant lies completely within the enveloping circular disk. In embodiments, the radial extent of the cross-sectional area can vary slightly especially along the central longitudinal axis. In such exemplary embodiments, the enveloping circular disk is definable with regard to the cross-sectional area having the maximum radial extent. Especially implants of the herein described form with conical inner cores, the opening angles of which are less than a few degrees, can be considered in the context of this specification to be implants, the radial extents of which exhibit only little change along the central longitudinal axis.

The above-described implant can, for example, be produced at least in part using conventional production processes, especially subtractive production processes. In this connection, possibilities include especially milling or other manufacturing methods of removal, such as especially laser cutting and/or laser ablation. In preferred embodiments, the implant is produced, at least in part and particularly preferably completely, by an additive production process (also: additive manufacturing process, 3D printing), especially by selective laser melting, selective laser sintering, electron beam melting or fused filament fabrication.

Production by such additive processes is advantageous especially in the case of implants having delicate structures, such as especially the aforementioned channel structure. Additive production processes are suitable especially for the production of implants composed of metallic or nonmetallic materials.

The surface of the implant is preferably structured in at least one structuring step during production. The structuring step encompasses, for example, subtractive or additive technologies. Subtractive techniques in this connection are, for example, removal processes. These include especially laser ablation, chemical etching of surfaces or treatment of the surface with an abrasive jet, especially a jet containing abrasive particles. Additive technologies include especially those suitable for depositing material, at least regionally, on the surface of the implant, such as, for instance, coating processes and/or processes for crystal deposition (discrete crystalline deposition). For the deposition of especially a flat layer, it is, for example, possible to anodize a metal surface of the implant. By means of the aforementioned additive or subtractive measures, it is especially possible to structure the surface such that the characteristic roughness thereof is within the submicrometer range, within the micrometer range and/or within the range between 10 µm and 100 µm (large micrometer range). Advantageously, various subtractive and/or additive technologies are combined together such that the surface of the implant has different roughnesses. For example, what can first be generated is a coarse-structured surface having a characteristic elevation profile within the range between 10 µm and 100 µm by blasting with a jet containing abrasive particles, which coarse-structured surface is then imprinted with a microstructuring within the micrometer range (for instance, within the range between 1 µm and 3 µm) by an etching or by multiple etchings, especially acid etchings. Alternatively or additionally, what can be generated is, for example, a structuring within the submicrometer range by specific deposition of single crystals, especially of hydroxyapatite. Chemical etchings are suitable especially for cleaning the surfaces in order to improve especially their hydrophilic properties, chemical activity or capacities for cell deposition for formation of bone tissue.

In embodiments, the aforementioned structuring steps are preferably carried out under a protective gas atmosphere in order to largely avoid contamination with foreign atoms.

A method for implanting the above-described implant into the human or animal body includes the following method steps:

a) providing an inlet, especially a minimally invasive inlet, for the site of implantation;
b) optionally removing bone material at the site of implantation, especially by drilling or chiseling;
c) optionally inserting a positioning aid, especially a guide pin or guide wire, at the site of implantation;
d) positioning the first end of the implant at the site of implantation, optionally with insertion of the guide pin or the guide wire into the passage opening of the implant;
e) driving the implant in the axial direction along the central longitudinal axis under the action of an axial force acting in the direction of the central longitudinal axis, especially by striking or hammering, into the bone material such that the implant penetrates, at least sectionally, the bones or bone fragments to be connected or to be stabilized;
f) optionally removing the positioning aid; and
g) optionally filling in the implant with filling material, especially cement, bone cement or artificial bone substitute material, in order to anchor the implant in the natural bone material.

In embodiments, the implant is driven in the axial direction along the central longitudinal axis under the action of an axial force acting solely in the direction of the central longitudinal axis such that the implant penetrates, at least sectionally, the bones or bone fragments to be connected or to be stabilized. In other words, when driving in the implant, no torque is exerted on the implant from the outside, as is customary when introducing screw implants for instance.

In one embodiment of the above-described method, the above method steps are repeated in order to place multiple implants next to one another, each bridging the bone parts to be connected. In this way, a relative rotation of the connected bone parts relative to one another is prevented effectively and the stability of the connection is improved. This is advantageous especially in the case of a procedure for the stabilization or fusion of the sacroiliac joint.

In embodiments of the method, what is introduced into the bones or bone fragments to be connected when removing the bone material is a bore, the length of which substantially corresponds to the axial length of the implant and the diameter of which maximally corresponds to the diameter of the inner core.

In other embodiments, the implant is inserted without prior removal of bone material. Here, for example, implants having a centering tip are driven, without predrilling, into the bone material of the bone parts to be connected at least under the action of an axial force directed along the central axis.

Other features which are considered as characteristic for the invention are set forth in the appended claims.

Although the invention is illustrated and described herein as embodied in an implant for the stabilization and/or fusion of the sacroiliac joint and a method for fixing the sacroiliac joint, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 3 is a side, perspective view of the implant from FIG. 1;
FIG. 4 is a top view of a first end of the implant from FIG. 1;
FIG. 5 is a top view of a second end of the implant from FIG. 1;
FIG. 12 is a perspective view of the inner core of a further possible embodiment of the implant;
FIG. 13 is a side view of the inner core from FIG. 12;
FIG. 14 is a sectional view of the inner core from FIG. 12;

DETAILED DESCRIPTION OF THE INVENTION

Parts which correspond to one another or are functionally identical are provided with the same reference signs in all the figures.

Referring now to the figures of the drawings in detail and first, particularly to FIGS. 1 to 4 thereof, there is shown an exemplary embodiment of the implant 100 according to the invention that is merely exemplary and not to be understood as restrictive and that is suitable especially for the stabilization and/or fusion of the sacroiliac joint.

Figure 1:
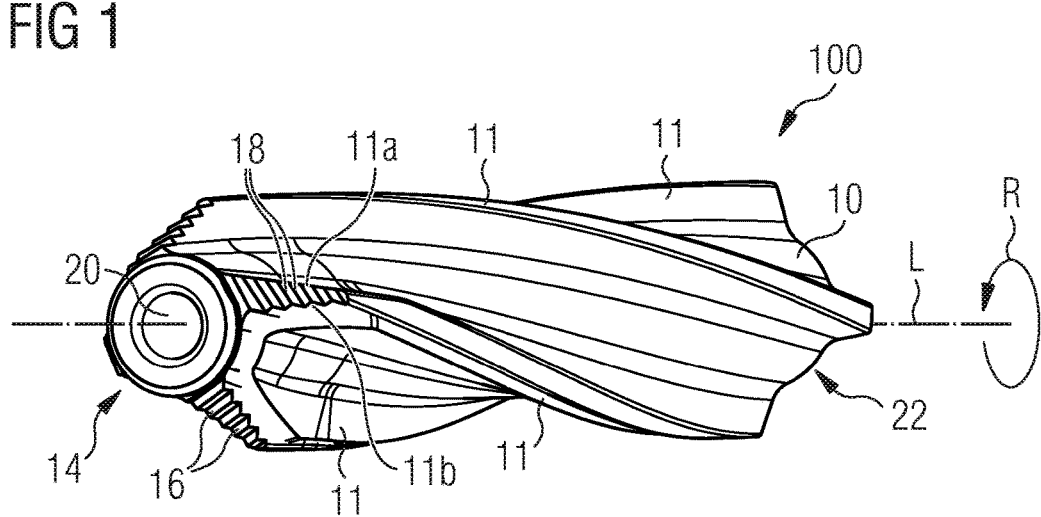
FIG. 1 is a diagrammatic, perspective view of an implant for a stabilization and/or fusion of a sacroiliac joint according to the invention.
Figure 2:
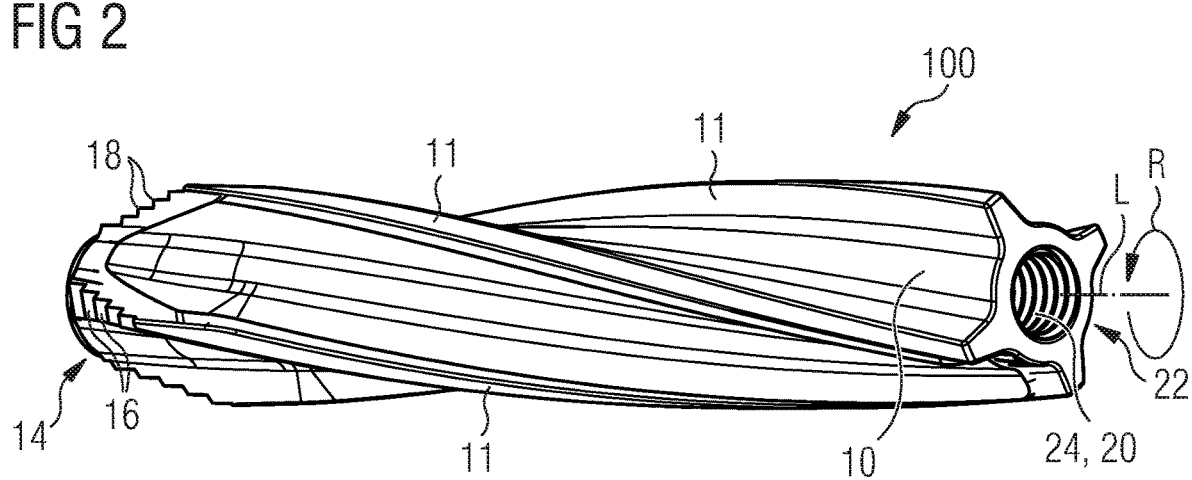
FIG. 2 is a perspective view of the implant from FIG. 1.

FIGS. 1 and 2 show perspective views of the implant 100. The depicted implant 100 consists of one piece and is solid in the exemplarily depicted embodiment. In other exemplary embodiments, the implant 100 has, for example, a channel structure containing multiple outwardly open channels or is formed from a porous material, meaning that an ingrowth of natural bone material is made possible.

The implant 100 if formed of, for example, a metal and is preferably formed by an additive manufacturing process, especially with the aid of selective laser sintering or selective laser melting. A surface of the implant 100 is preferably hydrophilic in order to promote an accumulation of cells especially for the formation of bone tissue.

The implant 100 is substantially pin-like or bolt-like and has an elongated shape extending in the axial direction along a central longitudinal axis L. The implant 100 contains an inner core 10 which is arranged around the central longitudinal axis L with rotational symmetry and is conically tapered, from which inner core four ribs 11 extend in the radial direction, which ribs are regularly spaced in the circumferential direction. In the cross section—as shown especially in FIGS. 2, 4 and 5—the implant 100 therefore has a star-shaped cross section.

The ribs 11 extend helically, i.e., spirally, around the central longitudinal axis L and substantially over the entire axial length of the implant 100. In particular, the ribs 11 form a right-handed helix in the depicted exemplary embodiment. In the region of a first end 14, the ribs 11 have a stepped profile which contains multiple steps 16. The widths of the steps 16 in the circumferential direction increase in the direction of the first end 14. Moreover, in the region of the first end 14, the inner core 10 is conically tapered. The implant 100 is configured to be driven into bone material with the first end 14 first. The orientation of the steps 16 or of step edges 18 in the region of the first end 14 is conceived for the geometric shape of the ribs 11: when the first end 14 is axially driven in the direction of the central longitudinal axis L into the bone material, what is brought about by the ribs 11 running diagonally in relation to the circumferential and axial direction is a force component or a torque in the direction of rotation of the helical ribs 11, i.e., a right-hand twist R directed clockwise (defined in the driving direction or infeed direction, i.e., when viewed along the central longitudinal axis L in the direction of the second end 22, FIG. 5) (cf. especially FIGS. 4 and 5). In the case of exemplary embodiments, the ribs 11 of which each form left-handed helices, the step edges 18 are accordingly oriented oppositely in order to generate a left-handed twist when driving the implant 100 into the bone material.

In the tapered region near the first end 14, the ribs 11 have an asymmetrical shape having a flat first flank 11a and a steep second flank 11b. The flat first flank 11a is oriented in the direction of the right-hand twist R in order to further facilitate a driving of the implant 100 under the action of an axial force.

In the case of exemplary embodiments, the ribs 11 of which form left-handed helices, the flanks 11a, 11b are accordingly arranged oppositely, i.e., the flat first flanks 11a are—when viewed along the central longitudinal axis L in the direction of the second end 22 of the implant 100—oriented counterclockwise in order to further facilitate a driving of the implant 100 under the action of an axial force.

The steep, second flank 11b can—as shown especially in FIG. 4—have a curvature.

The implant 100 further contains a passage opening 20 which extends substantially over the entire axial length of the inner core 10. When inserting the implant 100 at the site of implantation, the passage opening 20 serves for the accommodation of a previously placed guide pin or guide wire. At the second end 22 of the implant 100, which is arranged opposite the first end 14, the passage opening 20 is provided with an internal thread 24 into which an implantation tool having a complementarily formed external thread can be screwed. With the aid of the implantation tool, the already inserted implant 100 can be subsequently removed.

The exemplary embodiment depicted exemplarily in FIGS. 1 to 4 has a substantially smooth surface. Alternatively, the surface of the implant 100 is provided with a surface structuring, especially with a plurality of teeth or the like, in order to counteract movements of the implant.

The implant 100 is hollow. In advantageous exemplary embodiments, the inner core 10 and/or the ribs 11 can be porous or have a channel structure in order to make an ingrowth of natural bone material possible.

Owing to the spiraled exterior shape of the implant 100, movements of the bones or bone fragments fixed by the implant 100 are generally possible only under a relative rotation around the central longitudinal axis L. If the bones or bone fragments to be stabilized are fixed with the aid of multiple implants 100 arranged next to one another, such rotations are blocked effectively. Such measures can thus increase the stability of the connection mediated by the implant 100 and further limit the space for movement for the connected bone parts, and this can be advantageous especially in operations for the stabilization or fusion of the sacroiliac joint.

Possible variations with respect to the shape of the ribs 11 are illustrated especially in FIGS. 6 to 11. For better depiction of the ribs 11, FIGS. 6 to 11 show them without the inner core 10, the shape of which can likewise differ in different embodiments.

Figure 6:
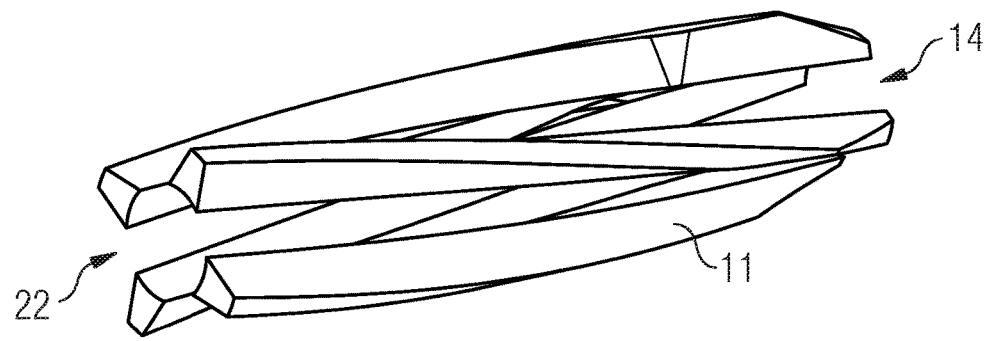
FIG. 6 is a perspective view of ribs of a possible embodiment of the implant.
Figure 7:
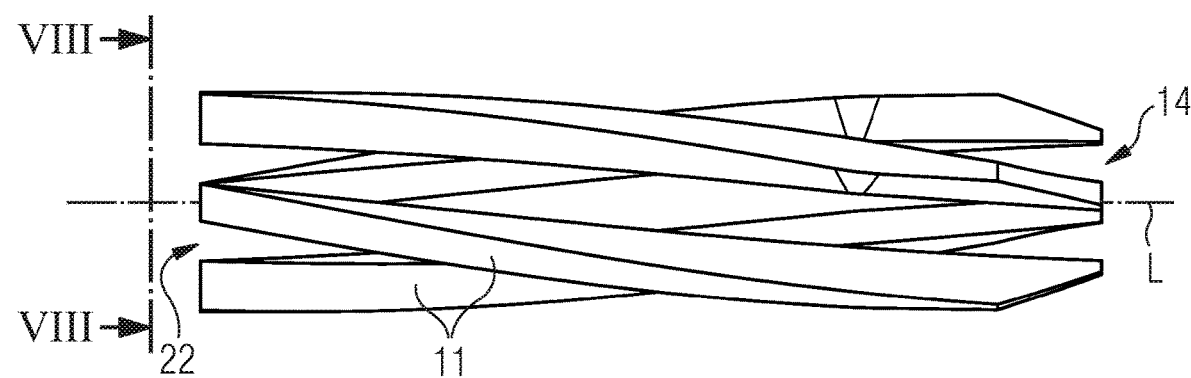
FIG. 7 is a side, perspective view of the ribs from FIG. 6.
Figure 8:
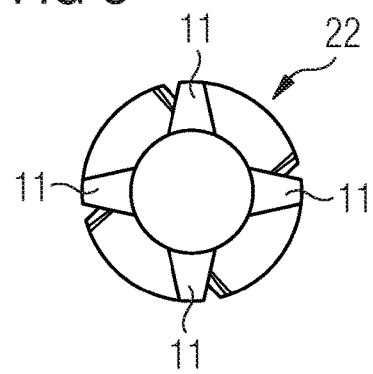
FIG. 8 is a top view in the direction of a central longitudinal axis of the ribs from FIG. 6.

FIGS. 6 to 8 illustrate different views of one possible variation of the ribs 11. Shown exemplarily is one embodiment having four ribs 11 which are regularly spaced from one another in the circumferential direction and which are trapezoidal in cross section (cf. especially FIGS. 6 and 8). Specifically, the ribs 10 have in cross section the shape of an isosceles trapeze. The ribs 10 extend substantially over the entire axial length of the implant and, while doing so, run spirally over an angular range of about 90° around the central longitudinal axis L.

Figure 9:
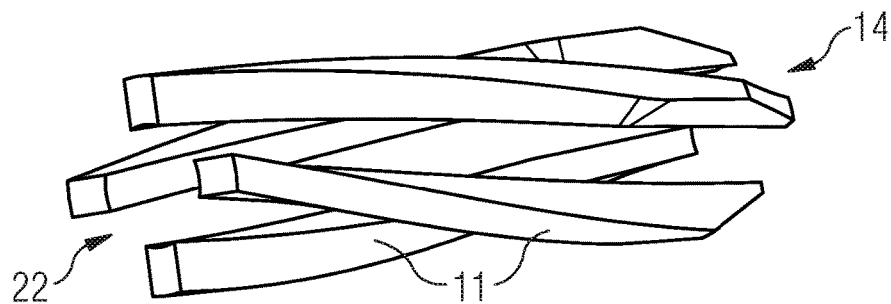
FIG. 9 is a perspective view of ribs of a further possible embodiment of the implant.
Figure 10:
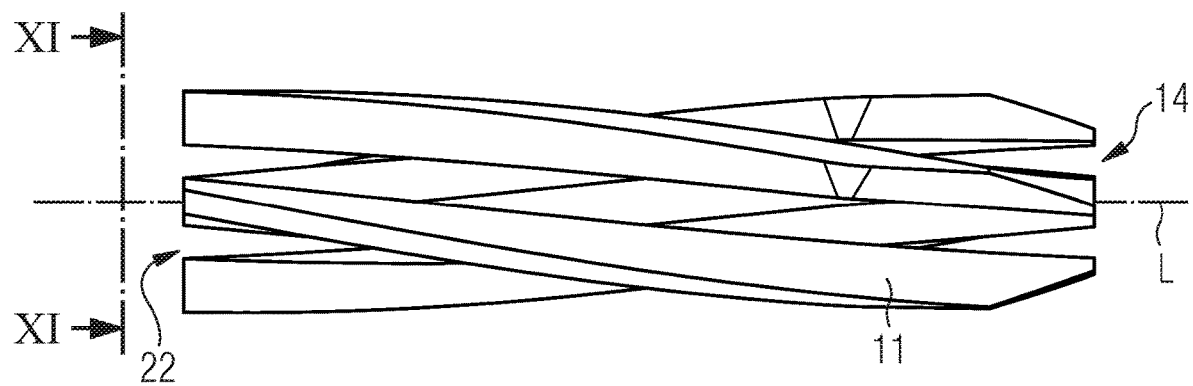
FIG. 10 is a side, perspective view of the ribs from FIG. 9.
Figure 11:
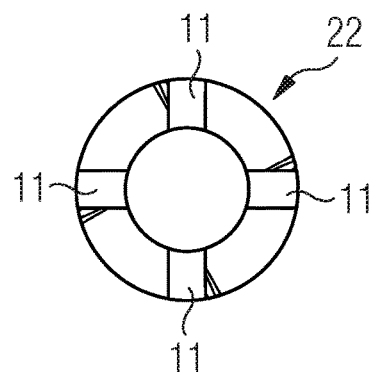
FIG. 11 is a top view in the direction of the central longitudinal axis of the ribs from FIG. 9.

FIGS. 9 to 11 illustrate different views of a further possible variation of the ribs 11. Shown exemplarily is one embodiment having four ribs 11 which are regularly spaced from one another in the circumferential direction and which are rectangular in cross section (cf. especially FIGS. 9 and 11). The ribs 10 extend substantially over the entire axial length of the implant and, while doing so, run spirally over an angular range of about 90° around the central longitudinal axis L.

The ribs 11 of the exemplary embodiments shown in FIGS. 6 to 11 taper toward the central longitudinal axis L in the region of the first end 14. The ribs 11 are smooth in the tapered region. In other embodiments, the ribs 11, as depicted exemplarily in FIGS. 1 to 4 for example, can be designed as a stepped profile comprising multiple steps 16 in the region of the first end 14.

Possible variations with respect to the shape of the inner core 10 are illustrated especially in FIGS. 12 to 14 in different views. For better depiction of the inner core 10, FIGS. 12 to 14 show it without ribs 11 arranged thereon, which ribs can have, for example, the shape shown in FIGS. 6 to 8 or 9 to 11.

The inner core 10 is rotationally symmetrical relative to the central longitudinal axis L and tapers conically in the direction of the first end 14. The opening angle W1 of the conical inner core 10 is, based on the central longitudinal axis, typically at most only a few degrees, and in possible embodiments even less than 1°, for example about 0.5°.

As shown in FIGS. 12 to 14, the inner core 10 contains, in possible exemplary embodiments, a further conical section having a different opening angle W2, which forms a centering tip 26 in the region near the first end 14. The region of the centering tip 26 is, for example, identical to the region in which the ribs 11 taper in the direction of the central longitudinal axis L. The opening angle W2 of the centering tip is greater than the opening angle W1 of the conical core 10. Based on the central longitudinal axis L, the opening angle W2 is, for example, less than 20°, preferably less than 15°. In the example depicted merely exemplarily in FIGS. 12 to 14 and not true to scale, the opening angle W2 of the centering tip 26 is approximately 10°.

Although the ribs 11 and the core 10 are depicted separately in FIGS. 6 to 14, it is evident that, in embodiments, these parts are produced as one piece, especially with the aid of an additive manufacturing process.

Figure 15:
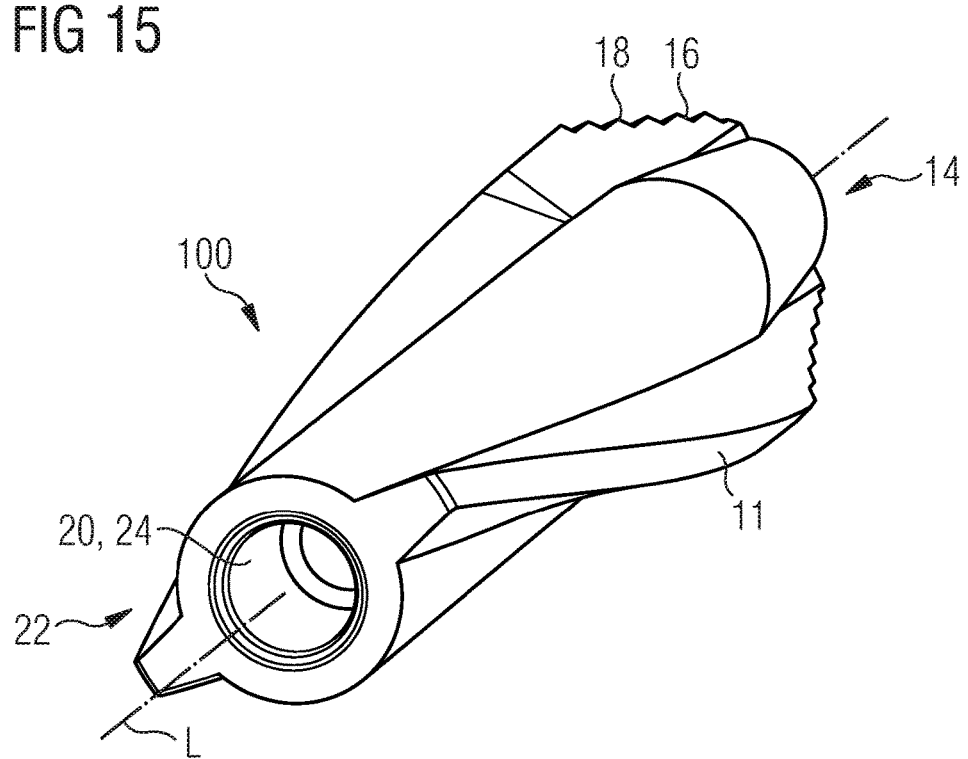
FIG. 15 is a perspective view of a further possible exemplary embodiment of the implant having two ribs arranged diametrically in relation to one another.
Figure 16:
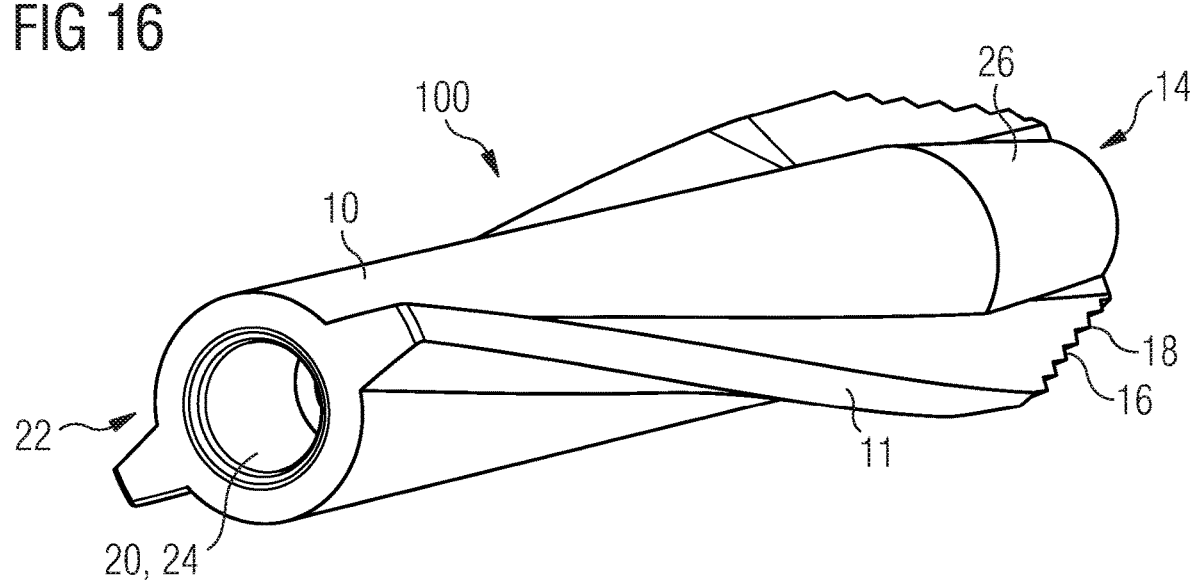
FIG. 16 is a further perspective view of the exemplary embodiment from FIG. 15.

FIGS. 15 and 16 show perspective views of a further exemplary embodiment, in which only two ribs 11 which are arranged diametrically in relation to one another and which protrude from the inner core 10 in the radial direction are provided. The ribs 11 extend over the entire axial length of the inner core 10 and altogether over an angular range of about 90° around the central longitudinal axis L. The thread pitch of the ribs 11 is thus relatively flat.

In possible exemplary embodiments, the thread pitch of the helical ribs 11 can be greater or smaller. In particular, the ribs 11 can extend over an entire angular range of less than 180°, for example over an angular range between 45° and 120°.

Figure 17:
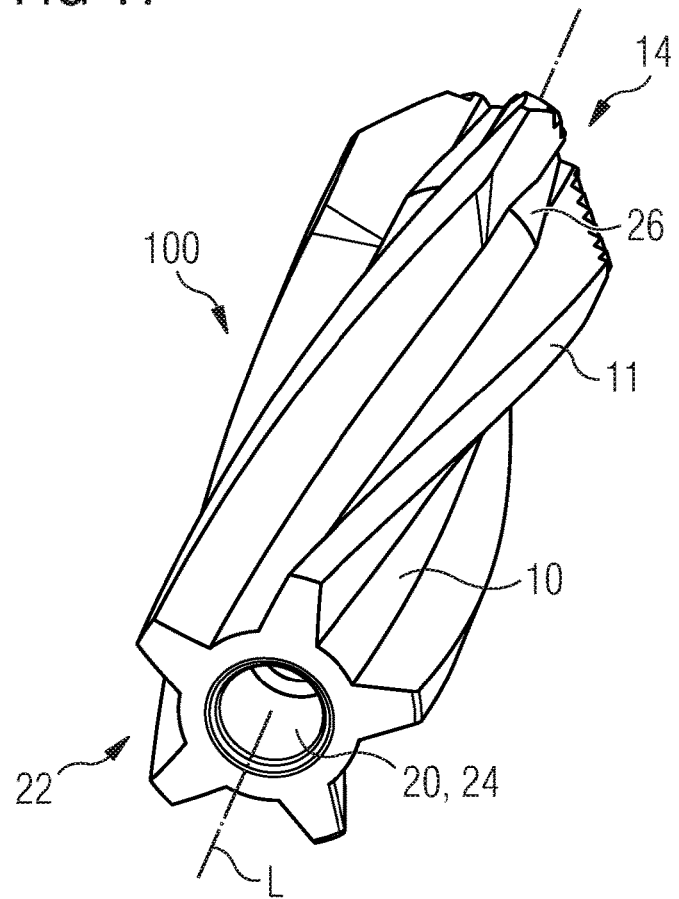
FIG. 17 is a perspective view of a further possible exemplary embodiment of the implant having five radially protruding ribs.
Figure 18:
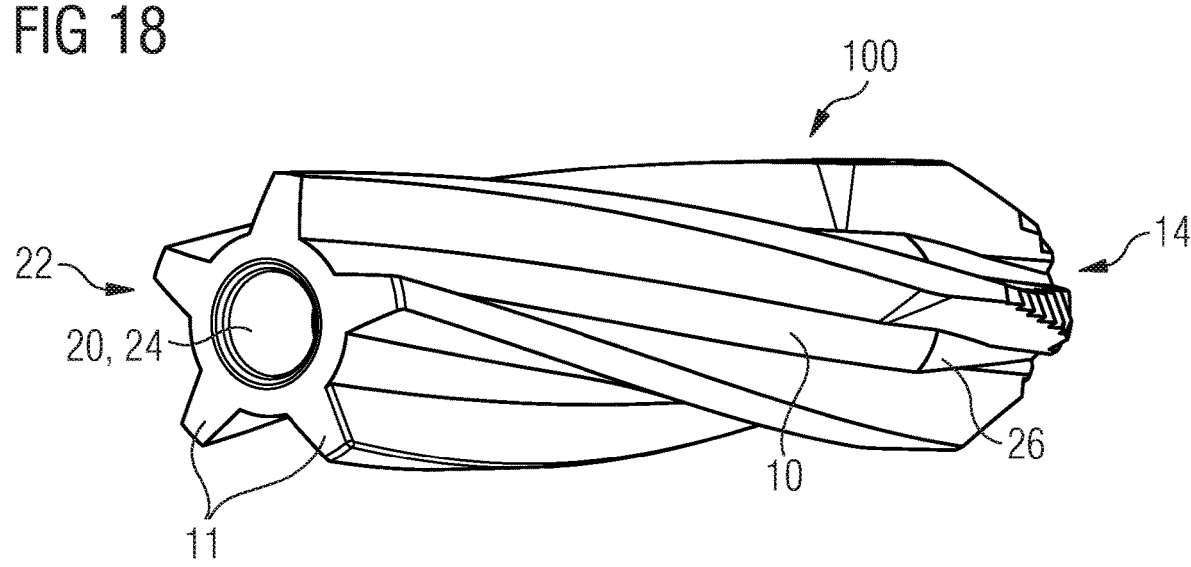
FIG. 18 is a further perspective view of the exemplary embodiment from FIG. 17.

FIGS. 17 and 18 show perspective views of a further exemplary embodiment, in which five ribs 11 which stick out radially from the inner core 10 and which extend spirally around the entire axial length of the core 10 are provided. In this connection, each rib 11 covers altogether an angular range of about 70° around the central longitudinal axis L.

FIGS. 19 to 22 show exemplary embodiments of the invention, in which the implant 100 is provided with channel structures 28 containing multiple channels 30. The channels 30 connect the passage opening 20 of the implant 100 to the outside and extend in the radial direction through the ribs 11 and/or the core 10.

Figure 19:
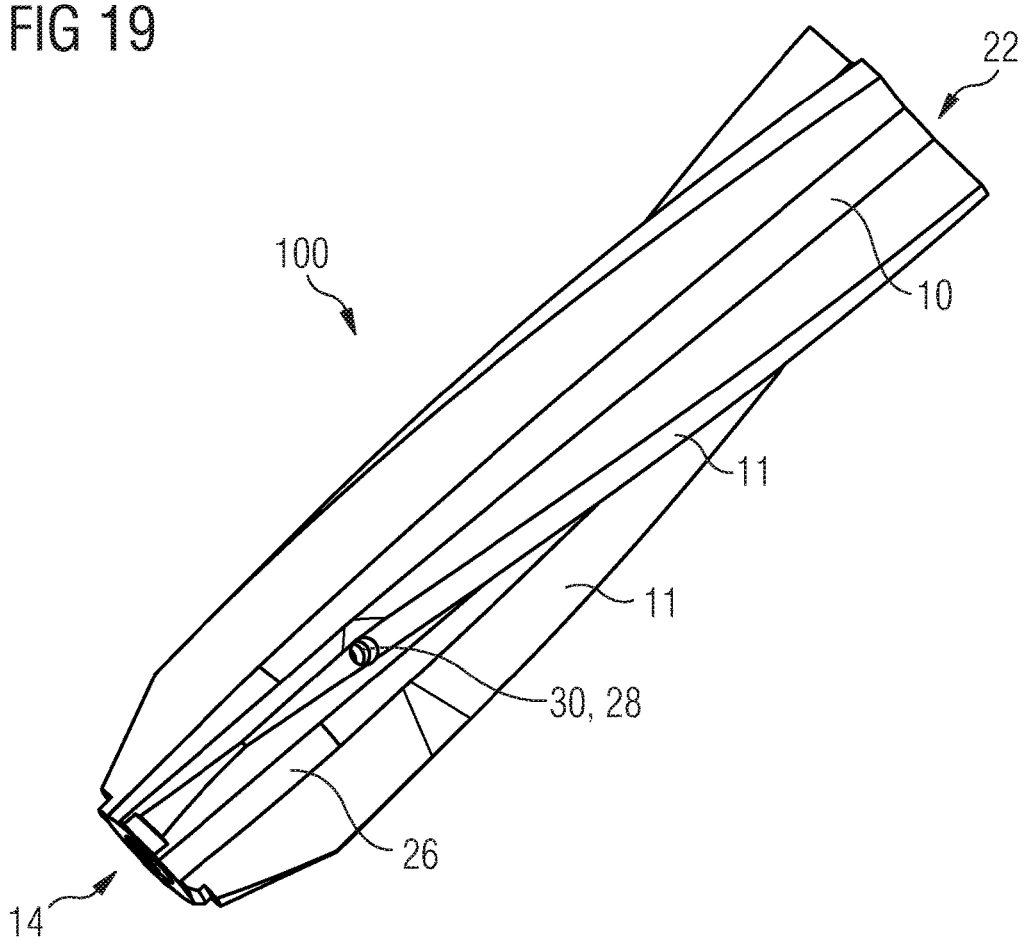
FIG. 19 is a perspective view of one exemplary embodiment of an implant having a channel structure.
Figure 20:
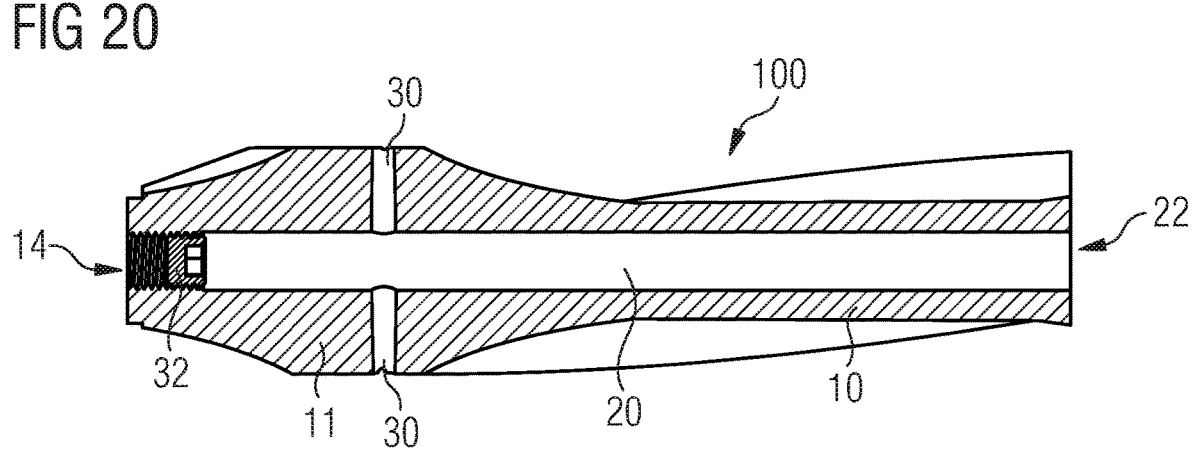
FIG. 20 is a sectional view of the exemplary embodiment from FIG. 19.
Figure 21:
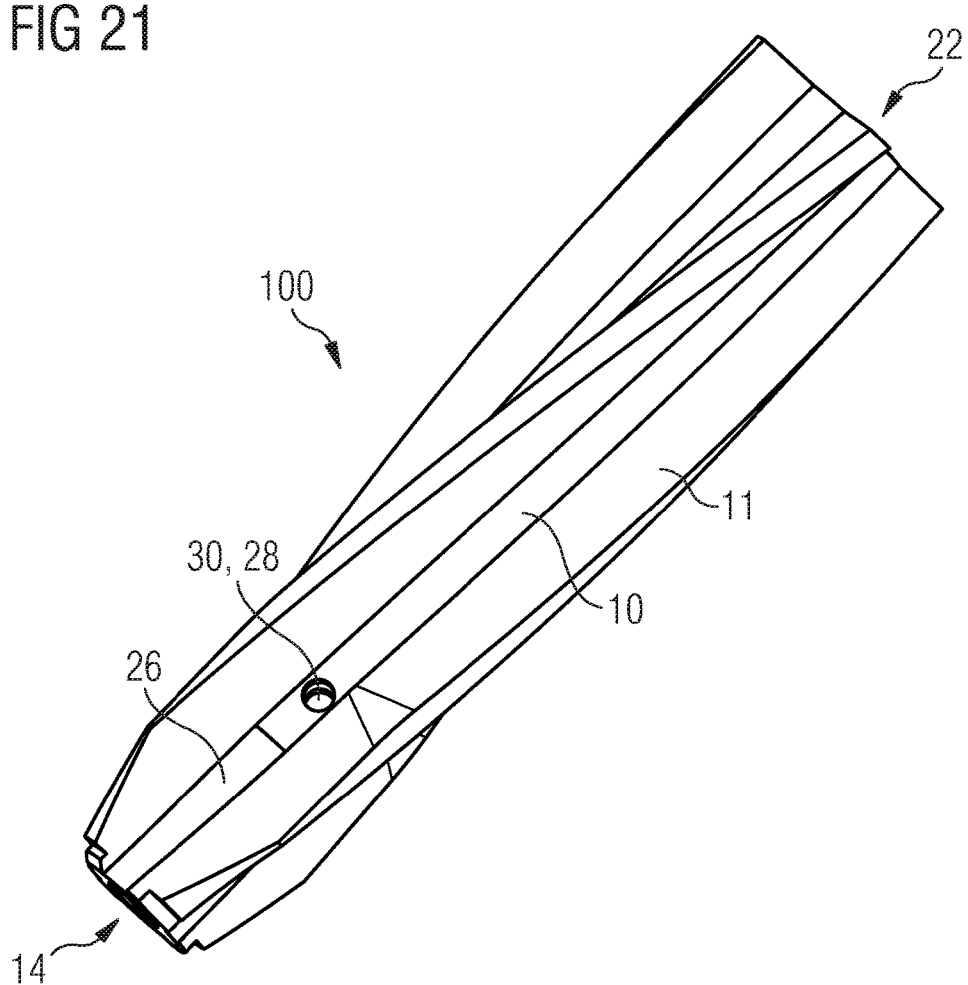
FIG. 21 is a perspective view of a further exemplary embodiment of an implant having a channel structure.
Figure 22:
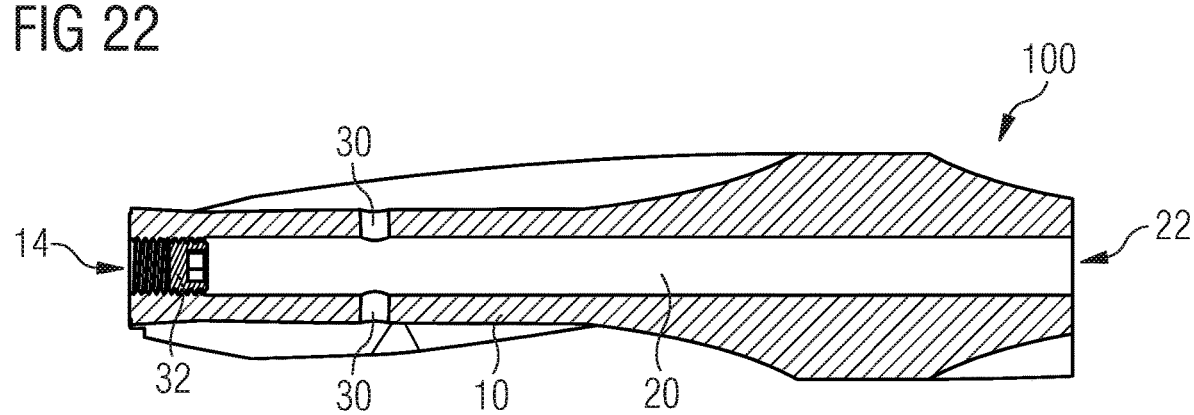
FIG. 22 is a sectional view of the exemplary embodiment from FIG. 21.

FIGS. 19 and 20 show one exemplary embodiment in which at least one channel 30 which extends in the radial direction through the rib 11 is provided. FIGS. 21 and 22 show a further exemplary embodiment in which at least one channel 30 which extends in the radial direction through the core 10 is provided. In general, both the core 10 and the ribs 11 can be provided with channels 30.

The exemplary embodiments of FIGS. 19 to 22 are especially intended to be filled in with bone cement or artificial bone substitute material in order to anchor the implant 100 at the site of implantation. So that the filling material escapes through the radial channels 30, the implant 100 is closable by a closing element 32 at the first end 14. In the exemplary embodiment depicted, the closing element 32 has, for this purpose, an external thread which engages in a corresponding internal thread, which is introduced internally in the passage opening in the region of the first end 14. After the insertion of the implant 100 into the bone material, the closing element 32 can be screwed in in order to close the front first end 14 of the passage opening 20.

In the case of the embodiments of the implant 100 that are shown exemplarily in FIGS. 15 to 22, centering tips 26 are provided for improved introduction of the implant 100 especially into bone material.

In the case of a method for implanting the implant 100 into the human or animal body, an inlet, for example a minimally invasive inlet, for the site of implantation is first provided. Optionally, bone material is removed at the site of implantation, especially by drilling or chiseling, for, for example, better positioning of the implant 100. However, this is generally not absolutely necessary, since the implant 100 is conceived to be directly driven into the bone material as a result of mediation of an axial force acting along the central axis L. Optionally, there is the possibility of the use of a positioning aid, such as, for instance, a guide pin or guide wire, which is introduced at the site of implantation beforehand and is subsequently inserted into the passage opening 20 of the implant 100.

The implant 100 is driven, with its first end 14 first, into the bone material in the axial direction under the action of an axial force, especially by striking or hammering. The inserted implant 100 penetrates, at least sectionally, the bones or bone fragments to be connected or to be stabilized and bridges especially the separation plane between the bones or bone fragments. Such a situation is depicted schematically in FIG. 23, where the bones are represented merely schematically by cuboids 110, 120. It is evident that the implant 100 is preferably completely driven into the bone material in the case of an actual surgical procedure.

Subsequently, the positioning aid is optionally removed and the implant is optionally filled in with filling material, especially cement, bone cement or artificial bone substitute material.

These steps are preferably repeated at least once, with the result that at least two implants 100 are inserted next to one another at the site of implantation.

The use of at least two implants 100 for the fixation of bone parts significantly improves the stability of the connection. Moreover, the geometric design of the implant 100 in possible embodiments is specifically adapted to anchoring in bone material. This shall be elucidated below with reference to FIGS. 23 and 24.

If the implant 100 is filled in with filling material, the implant 100 is closed terminally, optionally with the aid of the closing element 32, so that the filling material filled or injected into the passage opening 20 can escape across the channels 30 running radially, in order to thus combine with the surrounding bone tissue.

Figure 23:
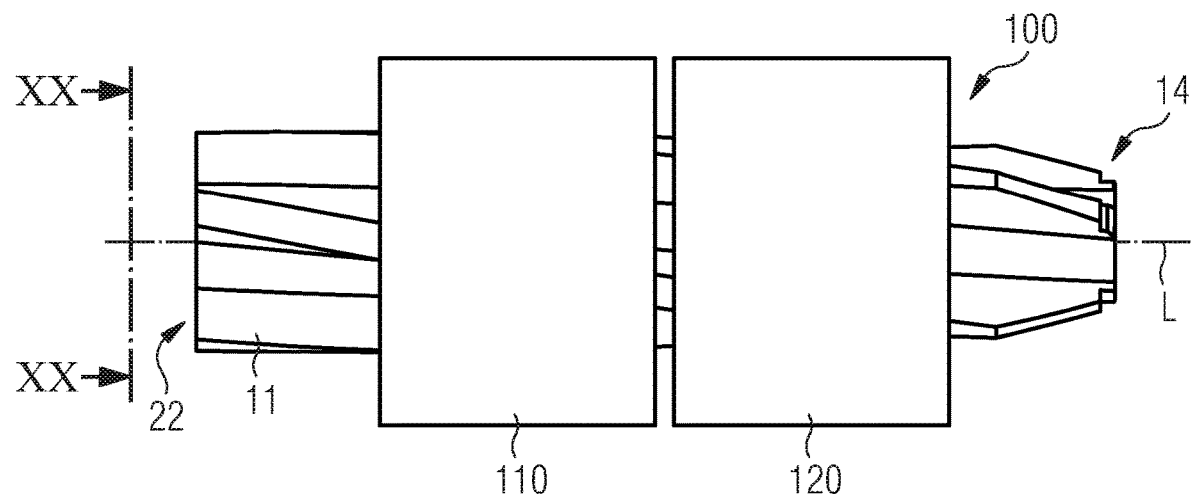
FIG. 23 is a side view of two parts connected by an implant.
Figure 24:
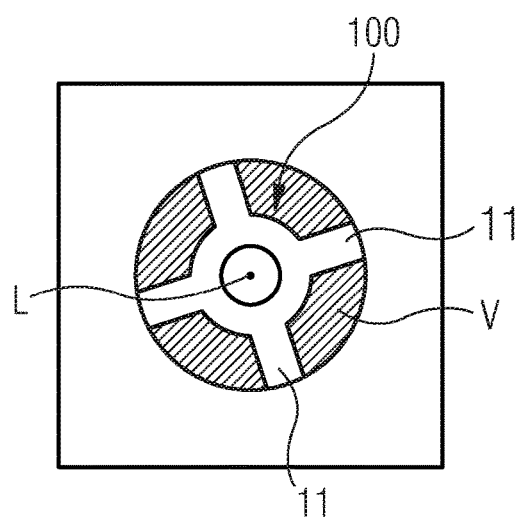
FIG. 24 is a top view in the direction of the central longitudinal axis of the two parts connected by the implant from FIG. 23.

FIGS. 23 and 24 illustrate schematically a side view and a top view of one situation, in which two cuboids 110, 120 are connected by an implant 100 configured according to the invention. Owing to the spiraled exterior shape of the implant 100, these two cuboids 110, 120 connected to one another can subsequently only then be moved apart in the axial direction without destruction if the translation in the axial direction is associated with a relative twist of the two cuboids 110, 120 relative to one another and around the longitudinal axis L of the implant 100. However, such a rotation of the cuboids 110, 120 relative to one another can, for example, be prevented or blocked by insertion of an additional implant 100, wherein the additionally introduced implant 100 likewise bridges a separation plane between the cuboids 110, 120.

The geometric dimensioning of the implant 100 can be specifically conceived for anchoring in bone material. It has become apparent that implants 100 suitable for this purpose can be characterized by the ratio between the volume of the ribs 11 and the displacement volume V, which substantially corresponds to the volume of the gaps between the ribs 11. In the case of typical materials for the implant 100, such as, for instance, metals, metal alloys, especially titanium alloys, for example Ti-6Al-4V or other metal alloys composed of titanium, zirconium, oxidized zirconium, hafnium, platinum, rhodium, niobium, medical-grade stainless steel, cobalt-chromium steel or tantalum, this ratio is within a range between 1:2 (1/2) to 1:10 (1/10), for example about 1:3 (1/3).

The volume of the ribs 11 is defined by the volume of the implant 100 minus the volume of the core 10 (cf. especially FIGS. 6 to 12 in relation to this).

The displacement volume V corresponds to the volume of the material which must be removed so that the implant 100 completely introduced into a material can be removed from the material by axial translation along the central longitudinal axis L. The displacement volume V is illustrated schematically in the cross-sectional picture in FIG. 24 and corresponds to the volume of a rotation body, which arises by continuous rotation of the implant 100 around the central longitudinal axis L, minus the volume of the implant 100. In cross section, it corresponds to the volume of the gaps which are delimited, in the circumferential direction, by the ribs 11 and, in the radial direction, by the core 10 and by a circular disk K enveloping the implant 100.

The implant 100 depicted especially in the figures is, for example, produced by means of conventional production processes, especially subtractive production processes, such as, for instance, milling. In embodiments, the implant 100 is produced by means of an additive production process. For example, the implant 100 is produced by selective laser melting, selective laser sintering, electron beam melting or fused filament fabrication. Thereafter, in embodiments, the surface of the implant is structured in at least one structuring step. The structuring step can, in particular, encompass various subtractive or additive technologies or combinations of subtractive or additive technologies. In embodiments, the surface of the implant 100 is roughened by treatment with a particle jet and then subjected to wet or dry chemical etching. Alternatively or additionally, what can be carried out is a microstructuring of the surface especially by laser ablation or a coating of the surface or a targeted application of material deposits to the surface, for example by means of single-crystal deposits. Such deposits consist of, for example, nonmetallic materials, such as, for instance, calcium phosphate or hydroxyapatite and/or a ceramic.

Although the invention has been more particularly illustrated and described in detail with regard to the depicted exemplary embodiments, the invention is not restricted thereby. Other variations and combinations can be derived therefrom by a person skilled in the art without departing from the essential concept of the invention. In particular, any combinations of features which have been described or disclosed with regard to various exemplary embodiments and/or figures are possible.

LIST OF REFERENCE SIGNS 10 inner core
11 rib
11a flank
11b flank
14 first end
16 step
18 step edge
20 passage opening
22 second end
24 internal thread
26 centering tip
28 channel structure
30 channel
32 closing element
100 implant
110 cuboid
120 cuboid
L central longitudinal axis
R right-hand twist
W1 opening angle
W2 opening angle
V displacement volume
K circular disk

The invention claimed is:

1. An implant for a stabilization and/or fusion of a sacroiliac joint and the implant having an elongated, spiraled exterior shape, the implant comprising:
  a conically tapered inner core with a passage opening formed therein and extending in an axial direction along a central longitudinal axis over an entire axial length of the implant; and
  ribs running outward in a radial manner at least sectionally and said ribs being disposed on said inner core and extending helically in the axial direction around at least one section of said inner core, said ribs taper, in a region of a first end of said conically tapered inner core, in a direction toward the central longitudinal axis and said ribs having, in said region of said first end, a terminal section having a stepped profile.

2. The implant according to claim 1, wherein said inner core has a centering tip which forms a terminally conically tapered section, an opening angle of said centering tip being greater than an opening angle of the conically tapered inner core and being based on the central longitudinal axis, less than 20°.

3. The implant according to claim 1, wherein said ribs taper in a region of a first end of said conically tapered inner core in a direction toward the central longitudinal axis.

4. The implant according to claim 1, wherein said stepped profile has multiple steps, widths of said steps increase in a circumferential direction in a direction of the first end.

5. The implant according to claim 1, wherein said ribs form a right-handed helix and said stepped profile has at least one step edge which, with regard to the axial direction and a circumferential direction, runs diagonally such that a right-hand twist is brought about when said terminal section is axially driven into bone material.

6. The implant according to claim 1, wherein said ribs form a left-handed helix and said stepped profile has at least one step edge which, with regard to the axial direction and a circumferential direction, runs diagonally such that a left-hand twist is brought about when said terminal section is axially driven into bone material.

7. The implant according to claim 1, wherein said conically tapered inner core is perforated.

8. The implant according to claim 1, wherein said conically tapered inner core has a channel structure.

9. The implant according to claim 1, wherein said ribs are perforated.

10. The implant according to claim 1, wherein said ribs have a channel structure.

11. The implant according to claim 8, wherein said channel structure has at least one outwardly open channel which provides a fluidic connection to said passage opening.

12. The implant according to claim 11, wherein said passage opening is closable by a closing element in a region of a first end of said conically tapered inner core.

13. The implant according to claim 1, wherein said conically tapered inner core has a surface structuring, said surface structuring having a specified roughness.

14. The implant according to claim 1, wherein said ribs have a surface structuring, said surface structuring having a specified roughness.

15. The implant according to claim 13, wherein said surface structuring contains, at least regionally, deposits consisting of a nonmetallic material.

16. The implant according to claim 1, wherein said ribs extending helically over the axial length of the implant wind around the central longitudinal axis over an angular range of less than 180°.

17. The implant according to claim 1, wherein said passage opening has, in a region of a second end of said conically tapered inner core, an internal thread for a screw-in of an implantation tool.

18. The implant according to claim 1, wherein a volume of said ribs and a displacement volume is in a ratio of from 1/10 to 1/2, the displacement volume corresponding to a difference between a volume of a rotation body, which arises by continuous rotation of the implant around the central longitudinal axis, and a volume of the implant.

19. A method for fixing a sacroiliac joint, which comprises the steps of:
providing at least one implant having an elongated, spiraled exterior shape, the implant containing a conically tapered inner core having a passage opening formed therein extending in an axial direction along a central longitudinal axis over an entire axial length of the implant and ribs running outward in a radial manner at least sectionally and the ribs are disposed on the inner core and extend helically in the axial direction around at least one section of the conically tapered inner core;
forming an inlet for a site of implantation;
positioning a first end of the implant at the site of implantation; and
driving in the implant in the axial direction along the central longitudinal axis under an action of an axial force acting in the direction of the central longitudinal axis such that the implant penetrates, at least sectionally, the bones or bone fragments to be connected or to be stabilized.

20. The method for fixing the sacroiliac joint according to claim 19, wherein the implant is one of at least two implants, and introducing the at least two implants next to one another under the action of axial forces acting in the direction of respective central longitudinal axes such that each of the implants penetrates, at least sectionally, the bones or the bone fragments to be connected or to be stabilized.

* * * * *